United States Patent [19]

Horodysky et al.

[11] Patent Number: 5,258,130
[45] Date of Patent: Nov. 2, 1993

[54] ANTIOXIDANT AND ANTIWEAR ADDITIVES FOR LUBRICANTS AND FUELS

[75] Inventors: Andrew G. Horodysky, Cherry Hill, N.J.; Shih-Ying Hsu, Morrisville, Pa.

[73] Assignee: Mobil Oil Corporation, Fairfax, Va.

[21] Appl. No.: 968,918

[22] Filed: Oct. 30, 1992

[51] Int. Cl.$^5$ ................ C10M 137/04; C10M 137/10
[52] U.S. Cl. ................... 252/42.7; 252/32.5; 252/46.4; 556/24; 556/25; 556/26
[58] Field of Search ............... 556/24, 25, 26; 252/42.7

[56] References Cited

U.S. PATENT DOCUMENTS

| | | | |
|---|---|---|---|
| 2,763,632 | 9/1956 | Johnson | 252/42.7 |
| 2,786,812 | 3/1957 | McDermott | 556/25 |
| 2,826,561 | 3/1958 | Gloskey | 252/42.7 |
| 3,296,193 | 1/1967 | Walsh et al. | 556/25 |
| 3,397,216 | 8/1968 | Welch et al. | 556/26 |
| 3,459,660 | 8/1969 | Shepherd | 252/42.7 |
| 3,467,683 | 9/1969 | Harson et al. | 556/26 |
| 4,071,545 | 1/1978 | Mihailovski | 556/25 |
| 4,551,258 | 1/1985 | Ikeda et al. | 252/32.7 |

OTHER PUBLICATIONS

Kirk-Othmer's Encyclopedia of Chemical Technology, vol. 16 pp. 573-579, John Wiley and Sons Publishers (1981).

*Primary Examiner*—Ellen M. McAvoy
*Attorney, Agent, or Firm*—Alexander J. McKillop; Malcolm D. Keen; Jessica M. Sinnott

[57] ABSTRACT

Reaction products of an organotin oxide, such as dibutyltin oxide, a diorgano dithiophosphoric acid such as di-(2-ethylhexyl)dithiophosphoric acid and an alkenyl or polyalkenyl succinic anhydride, such as dodecenyl succinic anhydride, are effective multifunctional antioxidant and antiwear additives in lubricants, greases and fuels.

29 Claims, No Drawings

ANTIOXIDANT AND ANTIWEAR ADDITIVES FOR LUBRICANTS AND FUELS

FIELD OF THE INVENTION

The invention relates to lubricants and fuels. More specifically, the invention relates to lubricant or fuel additives which have multifunctional antioxidant and antiwear properties which comprise the reaction product of an organotin compound, a hydrocarbyl-substituted succinic anhydride and a phosphoric acid compound.

BACKGROUND OF THE INVENTION

Under normal operating and storage conditions, lubricants are subject to high temperatures and oxygen which leads to their oxidation and decomposition. Oxidation of lubricants causes the build-up of oil-soluble acids, lacquers and sludge which contribute to serious damage to engines and other lubricated systems. Varnish and lacquer deposits form on hot metal surfaces that are exposed to the lubricant. These deposits are further oxidized to hard carbonacious materials. Antioxidant additives for lubricants have been described as improving the lubricant's thermal and oxidative stability which thereby enhances the ability of the lubricant to resist oxidation.

Additionally, the metal parts of mechanical systems under heavy loads and working under high performance conditions such as high speeds and temperatures will deteriorate due to the frictional forces created by relatively moving and bearing metal surfaces. Often, lubricants for such operations, i.e. high performance lubricants, do not prevent wear of the metal and as a result the performance of the system is adversely affected. It is desirable to blend additive packages containing antiwear additives with lubricants in order to prevent wear and increase the service and operating life of the machinery. In fuels, antiwear additives are used to prevent the wear of metal parts which have limited lubrication yet operate under high temperatures and high speeds as found; for example, in the fuel pump.

Zinc dithiophosphates are often described as having antioxidant and antiwear properties when used with various oleagenous compositions. However, zinc-containing additives are undesirable because of high costs associated with the production of zinc and undesirable environmental effects of zinc derivatives.

In U.S. Pat. No. 4,551,258 to Ikeda et al, dated Nov. 5, 1985, grease compositions containing the reaction products of zinc dithiophosphates, phosphoric acid esters and organotin compounds are disclosed as additives for greases.

Organotin compounds are described as high temperature stabilizers in polyvinylchloride (PVC) plastics especially rigid PVC as high temperature stabilizers in Kirk-Othmer's *Encyclopedia of Chemical Technology*, Vol. 16, pp 573-579, John Wiley and Sons Publishers (1981).

SUMMARY OF THE INVENTION

An improved multifunctional lubricant and fuel additive has now been found. The use of additive amounts of reaction products of a hydrocarbyl-substituted succinic anhydride, a phosphoric acid and an organometallic compound in automotive and industrial lubricants and fuels significantly enhances the thermal and oxidative stability, corrosion inhibiting, antirust, load-carrying, antifriction and/or antiwear properties of the fluids. These additives can extend the serviceable engine life and offer a zinc-free alternative to traditional zinc dithiophosphates. The additives also have the additional properties of friction reduction, cleanliness/detergency, antifatiguing, antiscuffing, antiscoring and antistaining. The invention is directed to a lubricant or fuel additives having multifunctional antioxidant/antiwear properties comprising the reaction product of an organotin compound, a phosphoric acid and a hydrocarbyl-substituted succinic anhydride, lubricant and fuel compositions containing the additive and methods of making the same. The carboxylates of the invention include phosphorus and sulfur atoms and have demonstrated superior antioxidant and antiwear properties.

The hydrocarbyl-substituted succinic anhydride starting materials are shown in the following structural formula:

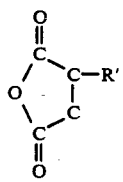

Where R' is a hydrocarbyl group containing 1 to 300 carbon atoms, preferably 6 to 150 carbon atoms. The hydrocarbyl group can be an alkenyl or polyalkenyl group which can, optionally, contain a heteroatom such as oxygen, nitrogen or sulfur. The hydrocarbyl-substituted succinic anhydride is made by known techniques, usually, by the reaction of a 1-olefin and maleic anhydride. Suitable 1-olefins include ethylene, propylene, butylene, isobutylene, pentylene, heptylene, decylene, dodecylene, eicosene, higher monoolefins, polymers and copolymers derived therefrom. The 1-olefin can also contain cyclic hydrocarbon groups such as phenyl, naphthyl or alicycle, heterocycles are also contemplated in which the heteroatom, such as oxygen, sulfur or nitrogen, is an integral part of a predominantly hydrocarbyl ring structure. In order to impart the beneficial solubility and emulsivity properties to the organic media in which the additive is used the hydrocarbyl group should have a molecular weight ranging from 50 to 2000, preferably from 100 to 1500.

The phosphoric acid is represented by the structural formula:

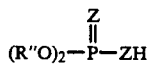

where R" is a hydrocarbyl group i.e., alkyl or aryl or a combination thereof such as aralkyl or alkaryl which contains 1 to 60 carbon atoms, preferably 1 to 20 carbon atoms, or R" is a hydrocarbyl group which contains 2 to 60 carbon atoms, preferably 2 to 20 and at least one heteroatom bonded to the hydrocarbyl group, the heteroatom can be oxygen, sulfur or nitrogen. The R" substituents falling within the above description can be the same or different. Z is a sulfur or oxygen atom. More preferably, at least 1, and most preferably, 2 Z's are sulfur. Phosphorus compounds contemplated include the phosphoric acid esters and dithiophosphoric acid esters such as di-(2-ethylhexyl) dithiophosphoric acid, dibutyl dithiophosphoric acid, diisobutyl dithiophosphoric acid, dioctyl dithiophosphoric acid, diamylphosphoric acid, dimethylphosphoric acid, diethyl phosphoric acid, di-n-propyl phosphoric acid, di-n-butyl phosphoric acid and dihexyl phosphoric acid. The dithiophosphoric acids are made by known methods, usually by treating $P_4S_{10}$ with alcohols, phenols or naphtols, or any other suitable hydroxyhydrocarbyl, hydroxyaliphatic, hydroxyaryl or hydroxyalkylaryl compounds.

The succinic anhydride and the phosphoric acid react to form an intermediate. Thereafter, the organotin compound is reacted with the succinic anhydride derivative to produce the final product.

The organotin compound can be made by known processes which are described in Kirk-Othmer *Encyclopedia of Chemical Technology*, Vol. 16, p. p. 573-579, John Wiley and Sons Publishers (1981) which is incorporated herein by reference. Essentially the process of making the organotin compound involves alkylation of tin tetrachloride with a suitable alkylating agent such as the Grignard Reagent, represented by the formula $R_1MgCl$, where $R_1$ is a hydrocarbyl or the direct reaction of tin with alkyl halides.

The organotin compound is a substituted organotin generally represented by the structural formula:

$$R_aSn(Y)_{4-a}$$

where R is a hydrocarbyl group, a is an integer ranging from 1 to 3 and Y is an oxygen atom or a sulfur atom. Y can also be a halogen such as fluorine, chlorine, bromine or iodine. The hydrocarbyl group designated by R is an alkyl or polyalkyl group which can be any paraffinic hydrocarbon radical, represented by the general formula $C_nH_{2n+1}$ where n ranges from to 20, preferably 4 to 18. The hydrocarbyl group can also be an alkenyl or polyalkenyl or aryl group which is a ring structure characteristic of the phenyl, naphthyl, phenanthryl and anthryl groups R can also be a combination of alkyl and aryl such as aralkyl or alkaryl. Non-limiting examples of suitable organotin compounds include dibutyltin oxide, dibutyltin dichloride, dioctyltin oxide, dioctyltin dichloride, dimethyltin oxide, dimethyltin dichloride, tributyltin oxide, tributyltin chloride, triphenyltin oxide, triphenyltin chloride, trioctyltin chloride and monooctyltin trichloride.

The reactants combine in stoichiometric proportions such that one equivalent amount of each of the hydrocarbyl-substituted succinic anhydride and the dithiophosphoric acid react with the organotin compound. However, an excess of one reactant over another can be used. The resulting products are varied and complex in structure; however, although not bound by the mechanism it is believed that when the di-substituted organotin compound is used the reaction can be generalized by the illustrative mechanism which follows:

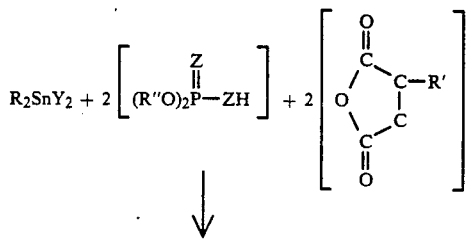
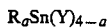
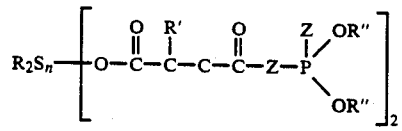

Where R, R', R", Y and Z are as defined above.

The reactants can be contacted at ambient pressure and temperatures ranging from at least 0° C. to 15° C., at most from 110° C. to 150° C. As mentioned above, the reactants combine stoichiometrically, thus, an excess of one reactant, over the other can be used. Generally, the reactants can be combined in any sequence. Preferably, the reactants are combined batchwise and contacted for at least 15 minutes to 1 hour and up to 4 hours to 24 hours or more. A solvent or diluent inert to the reactants can be optionally used to facilitate the reaction. Examples of suitable solvents include toluene, xylenes or hexane. The reactants combine into an effective composition which retains the beneficial additive characteristics of the starting materials and also acquires new synergistic antioxidant properties.

When the organotin halide is used the reaction mixture includes an acid scavenging compound such as a tertiary amine, i.e. triethylamine. The acid scavenging compound is added to the mixture at the same time as the other reactants. The acid scavenger can be left out of the reaction mixture but the product will not work as effectively in fuel and lubricant applications.

The additives are most effective in industrial lubricating applications where large charges of oil are expected to last the lifetime of the machinery without being replaced. The antioxidant additives of the present invention are particularly necessary in this respect because throughout the serviceable life, the oil is exposed to oxidizing conditions such as circulating air, water and metal oxidation products resulting from the wear of metal surfaces.

Gas turbine engines require multifunctional lubricant additives of the type herein described. The temperature ranges, contamination and oxidation conditions to which the lubricant is exposed can be such that oil deterioration can be rapid.

The additives are also useful in diesel engine oils, i.e., those used in marine diesel engines, locomotives, power plants and high speed automotive diesel engines. These multifunctional antioxidants can be particularly useful in diesel engines because the engines do not combust as cleanly or completely as gasoline engines. Oil degradation in service is a consequence of oxidative breakdown from blow-by gases containing high concentrations of oxides of nitrogen which promote oil oxidation and accelerate oil thickening. Additionally, metallic contaminants from metals commonly present in these engines such as copper, lead and iron catalyze oxidation.

Gasoline burning engines also benefit from the additives of the invention, although they can be, under certain circumstances, easier to lubricate than comparable diesel engines, because of cleaner combustion and, occasionally, less demanding operating conditions. However, since engine efficiency is ever-increasing in order to conserve scarce resources, the need for multifunctional engine lubricant additives which improve resistance to corrosion, oxidation and wear predominates.

Automatic transmission fluids are another class of lubricants which benefit from the additives of the present invention. These fluids represent a careful balance of properties needed to meet the unique requirements of automatic transmissions. Improved oxidation stability, extra corrosion protection and antiwear properties are particularly important and necessary properties of these fluids. Hydraulic fluids in industrial equipment and air compressors have similar requirements and, thus, these additives are also beneficial in these fluids.

Gear oils are another class of fluids which would benefit from the additives of the present invention. Typical of such oils are automotive spiral-bevel and worm-gear axle oils which operate under extreme pressures, load and temperature conditions which require antiwear additives. Additionally, hypoid gear oils operating under both high speed, low-torque and low-speed, high torque conditions require lubricants that contain the multifunctional antiwear additives of the present invention. When these gear oils are in service they are in intimate contact with air, making them prone to oxidation which leads to decomposition and polymerization products.

In general, the mineral oils, both paraffinic and naphthenic and mixtures thereof can be employed as a lubricating oil or as the grease vehicle. The lubricating oils can be of any suitable lubrication viscosity range, for example, from about 45 SUS at 100° F. to about 6000 SUS at 100° F., and preferably from about 50 to 250 SUS at 210° F. Viscosity indexes from about 70 to 95 are preferred. The average molecular weights of these oils can range from about 250 to about 800.

Where synthetic oils, or synthetic oils employed as the vehicle for the grease, are desired in preference to mineral oils, or in mixtures of mineral and synthetic oils, various synthetic oils may be used. Typical synthetic oils include polyisobutylenes, polybutenes, hydrogenated polydecenes, polypropylene glycol, polyethylene glycol, esters, hydrogenated synthetic oils, polyphenyls, siloxanes and silicones (polysiloxanes) and alkyl-substituted diphenyl ethers.

Where the lubricant is employed as a grease, the lubricant is generally used in an amount sufficient to balance the total grease composition, after accounting for the desired quantity of the thickening agent, and other additive components included in the grease formulation. A wide variety of materials can be employed as thickening or gelling agents. These can include any of the conventional metal salts or soaps, such as calcium, or lithium stearates or hydroxystearates, which are dispersed in the lubricating vehicle in grease-forming quantities in an amount sufficient to impart to the resulting grease composition the desired consistency. Other thickening agents that can be employed in the grease formulation comprise the non-soap thickeners, such as surface-modified clays and silicas, aryl ureas, calcium complexes and similar materials. In general, grease thickeners can be employed which do not melt or dissolve when used at the required temperature within a particular environment; however, in all other respects, any material which is normally employed for thickening or gelling hydrocarbon fluids for forming greases can be used in the present invention.

The additives are particularly useful in greases used in automobile chassis lubrication. Chassis lubricants need the multifunctional additives primarily because the machinery is exposed to many environments and extreme conditions, i.e., high and low temperatures, rain, mud, dust, snow and other conditions such as road salts and road conditions. The additives of the invention are necessary to provide improved rust protection, better oxidation and mechanical stability, reduced fretting and corrosion and improved load carrying capability.

The lubricating oils and greases contemplated for blending with the reaction product can also contain other additive materials such as corrosion inhibitors, detergents, extreme pressure agents, viscosity index improvers, co-friction reducers, co-antiwear agents, co-antioxidants and the like.

The additives can be blended in a concentration from at least 0.01 wt. % to about 0.3 wt. % to at most 5 wt. % to about 10 wt. % based on the total weight of the lubricant composition.

The additives are also useful in fuels. When the additives are utilized in fuels, the fuels contemplated are liquid hydrocarbon and liquid oxygenated fuels such as alcohols and ethers. The additives are blended in a concentration from about 25 to about 500 pounds of additive per 1000 barrels of fuel.

Specifically, the fuel compositions contemplated include gasoline base stocks such as a mixture of hydrocarbons boiling in the gasoline boiling range which is from about 90° F. to about 450° F. This base fuel may consist of straight chains or branched chains or paraffins, cycloparaffins, olefins, aromatic hydrocarbons, or mixtures thereof. The base fuel is derived from among others, straight run naphtha, polymer gasoline, natural gasoline or from catalytically cracked or thermally cracked hydrocarbons and catalytically cracked reformed stock. The composition and octane level of the base fuel are not critical and any conventional motor fuel base is employed in the practice of this invention. Further examples of fuels of this type are petroleum distillate fuels having an initial boiling point from about 75° F. to about 135° F. and an end boiling point from about 250° F. to about 750° F. It should be noted in this respect that the term distillate fuels is not intended to be restricted to straight-run distillate fractions. These distillate fuel oils are straight-run distillate fuel oils catalytically or thermally cracked (including hydrocracked) distillate fuel oils etc. Moreover, such fuel oils are treated in accordance with well-known commercial methods, such as acid or caustic treatment dehydrogenation, solvent refining, clay treatment and the like.

Particularly contemplated among the fuel oils are Nos. 1, 2 and 3 fuel oils used in heating and as Diesel fuel oils, gasoline, turbine fuels and jet combustion fuels.

The fuels can contain alcohols and/or gasoline in amounts or 0 to 50 volumes per volume of alcohol or the fuel can be an alcohol-type fuel containing little or no hydrocarbon. Typical of such fuels are ethers and alcohols such as methanol, ethanol and mixtures of methanol and ethanol. The fuels which are treated with the additive include gasohols which are formed by mixing 90 to 95 volumes of gasoline with 5-10 volumes of ethanol or methanol. A typical gasohol contains 90 volumes of gasoline and 10 volumes of absolute ethanol.

The fuel compositions of the instant invention additionally comprise any of the additives generally employed in fuel compositions. Thus, compositions of the instant invention additionally contain conventional carburetor detergents, anti-knock compounds such as tetraethyl lead, anti-icing additives, upper cylinder and fuel pump lubricity additives and the like.

The foregoing examples illustrate the possible methods of preparing the additive product of the invention.

EXAMPLE 1

A solution of di-(2-ethylhexyl)dithiophosphoric acid (23 g, 0.065 mol) was added dropwise to a stirred solution of dodecenyl succinic anhydride (17.3 g, 0.065 mol) in toluene or xylenes. The resulting solution was refluxed for one hour and cooled to ambient temperature. This was followed by addition of dibutyltin oxide (8.1 g, 0.032 mol). The mixture was refluxed for one hour or until 0 58 ml $H_2O$ was collected in a Dean-Stark trap. The solvent was evaporated under reduced pressure to afford a brownish oil (47 g).

The organotin compounds obtained according to the above-described method exhibited very good multipurpose antioxidant and antiwear properties in mineral based lubricants under both the mild and severe mechanical conditions. The additive not only enhances the thermal and oxidative stability of premium quality automotive and industrial lubricants and extends the service life of these organic fluids but it also offers a zinc-free alternative to zinc dithiophosphates.

EVALUATION OF THE PRODUCT

The reaction product of Example 1 was blended in a concentration of 1 wt % in a 200 second solvent refined, paraffinic, neutral mineral oil and evaluated for antioxidant performance in the Catalytic Oxidation Test at 325° F. for 40 hours (Table 1) and in the Catalytic Oxidation Test at 325° F. for 72 hours (Table 2). For comparative purposes, the oxidation-inhibiting test results of commercial, traditional phenolic and arylamine antioxidants were reported in Tables 1 and 2 along with the superlative test results achieved by the additive of the invention.

The Catalytic Oxidation Test procedures consisted of subjecting a volume of the test lubricant to a stream of air which was bubbled through the test composition at a rate of about 5 liters per hour for the specified number of hours and at the specified temperature. Present in the test composition were metals frequently found in engines, namely:

1) 15.5 square inches of a sand-blasted iron wire;
2) 0.78 square inches of a polished copper wire;
3) 0.87 square inches of a polished aluminum wire; and
4) 0.107 square inches of a polished lead surface.

The results of the tests were presented in terms of percent change in kinematic viscosity ($\Delta KV$) and change in neutralization number ($\Delta TAN$). Essentially, the small percentage of change in KV meant that the lubricant maintained its internal resistance to oxidative degradation under high temperatures, the small change in TAN indicated that the oil maintained its low acidity level under oxidizing condition.

TABLE 1

| Item | Catalytic Oxidation Test 40 hours at 325° | | |
|---|---|---|---|
| | Additive Conc. (wt. %) | Change in Acid Number $\Delta$ TAN | % Change in Viscosity $\Delta$ KV |
| Base Oil (200 second, solvent refined, paraffinic neutral, mineral oil) | none | 16.68 | 326 |
| Commercially Obtained Arylamine Antioxidant (Ciba Geigy "Irganox L-57") (in above oil) | 1.0 | 7.08 | 36.9 |
| Commercially Obtained Phenolic Antioxidant (Ethyl Corp. "Ethyl 702") (in above oil) | 1.0 | 5.33 | 49.6 |
| Example 1 (in above oil) | 1.0 | 1.58 | 15.8 |

TABLE 2

| Item | Catalytic Oxidation Test 72 hours at 325° | | |
|---|---|---|---|
| | Additive Conc. (wt. %) | Change in Acid Number $\Delta$ TAN | % Change in Viscosity $\Delta$ KV |
| Base Oil (200 second, solvent refined, paraffinic neutral, mineral oil | none | 22 | 410 |
| Commercially Obtained Arylamine Antioxidant (Irganox L-57) (in above oil) | 1.0 | 8.75 | 65.3 |
| Commercially Obtained Phenolic Antioxidant (Ethyl 702) (in above oil) | 1.0 | 9.36 | 82.3 |
| Example 1 (in above oil) | 1.0 | 4.37 | 29.7 |

The ability of the oil containing the additives of the present invention to prevent the wearing down of metal parts under sever operating conditions was tested in the ASTM D2266 Shell 4-Ball Wear Test. The results of the test were presented in Table 3. Following the standard ASTM testing procedure, the test apparatus was a device comprising four ¼ inch steel balls three of which were in contact with each other in one plane in a fixed triangular position in a reservoir containing the test sample which was 1.0 wt % by weight of the total composition of the product of Example 1 blended into a base oil which was a mixture of an 80% solvent paraffinic bright (a high viscosity, fully refined and dewaxed lubricating oil traditionally used for blending with lower viscosity oils) and a 20% solvent paraffinic neutral lubricant oil (a purified, dewaxed lubricating oil stock traditionally blended with a bright stock to make a high quality lubricating oil). The fourth ball was above and in contact with the other three. The fourth ball was rotated at 2000 rpm while under an applied load of 60 kg, which pressed it against the three balls with pressure applied by weight and lever arms. The tests were conducted at 200° F. for 30 minutes. The diameter of the scar on the other three lower balls was measured with a low power microscope and the average diameter measured in two directions on each of the three lower balls was taken as a measure of the antiwear characteristics of the test composition. Table 3 showed the marked decrease in wear scar diameter obtained with respect to the test composition containing the product of Example 1.

TABLE 3

| | Four Ball Wear Test 60 kg/2000 rpm/30 min/200° F. | |
|---|---|---|
| Item | Additive Concentration (%) | Wear Scar (mm) |
| Base Oil (80% solvent paraffinic bright, 20% neutral lubricant oils) | none | 3.96 |
| Example 1 (in above oil) | 1.0 | 1.86 |

From the data presented in Tables 1, 3 & 3, it was clear that the compound of the invention was both an excellent antioxidant an antiwear additive.

We claim

1. A lubricant or fuel additive having multifunctional antioxidant/antiwear properties comprising a reaction product made by reacting a hydrocarbon substituted phosphoric acid and a hydrocarbon substituted succinic anhydride to produce an intermediate which is post-reacted with a hydrocarbon substituted organotin compound.

2. The reaction product of claim 1 in which the organotin compound has the formula:

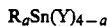

where R is a hydrocarbyl group containing 2 to 20 carbon atoms, a is an integer ranging from 1 to.3, and Y is an oxygen atom or a sulfur atom.

3. The reaction product of claim 2 in which the organotin compound is dibutyltin oxide, dimethyltin oxide, tributyltin oxide dioctyltin oxide or triphenyltin oxide.

4. The reaction product of claim 1 in which the phosphoric acid is represented by the structural formula:

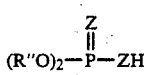

where R" is a hydrocarbyl group containing 1 to 60 carbon atoms or a hydrocarbyl group containing 2 to 60 carbon atoms and one or more heteroatoms selected from the group consisting of oxygen, sulfur or nitrogen and Z is a sulfur atom or an oxygen atom.

5. The reaction product of claim 4 in which the phosphoric acid compound is a phosphoric acid ester or a dithiophosphoric acid ester.

6. The reaction product of claim 5 in which the phosphoric acid compound is di-(2-ethylhexyl) dithiophosphoric acid, dibutyl dithiophosphoric acid, diamylphosphoric acid, diisobutyl dithiophosphoric acid, dihexylphosphoric acid, dimethyl phosphoric acid, diethyl phosphoric acid, di-n-propyl phosphoric acid, di-n-butyl phosphoric acid or dioctyl dithiophosphoric acid.

7. The reaction product of claim 1 in which the hydrocarbyl-substituted succinic anhydride has the following structural formula:

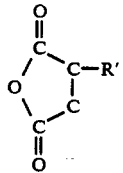

where R' is a hydrocarbyl group containing 1 to 300 carbon atoms.

8. The reaction product of claim 7 in which the hydrocarbyl-substituted succinic anhydride is made from a 1-olefin and maleic anhydride, the 1-olefin being ethylene, propylene, butylene, isobutylene, pentylene, heptylene, decylene, dodecylene, eicosene, higher mono-olefins, polymers and copolymers derived therefrom or any of the foregoing olefins containing cyclic hydrocarbon groups such as phenyl, naphthyl or alicycle, the hydrocarbyl group having a molecular weight ranging from 50 to 2000.

9. A lubricating oil composition comprising a major amount of a lubricating oil and a minor multifunctional antioxidant/antiwear amount of a reaction product made by reacting a hydrocarbon-substituted phosphoric acid and a hydrocarbon-substituted succinic anhydride to produce an intermediate which is post-reacted with a hydrocarbon-substituted organotin compound.

10. The composition of claim 9 in which the organotin compound has the formula:

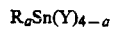

where R is a hydrocarbyl group containing 2 to 20 carbon atoms, a is an integer ranging .from 1 to 3, and Y is an oxygen atom or a sulfur atom.

11. The composition of claim 9 in which the organotin compound is dibutyltin oxide, dimethyltin oxide, tributyltin oxide, dioctyltin oxide or triphenyltin oxide.

12. The composition of claim 9 in which the phosphoric acid is represented by the structural formula:

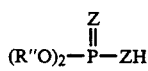

where R" is a hydrocarbyl group containing 1 to 60 carbon atoms or a hydrocarbyl group containing 2 to 60 carbon atoms and one or more heteroatoms selected from the group consisting of oxygen, sulfur or nitrogen and Z is a sulfur atom or an oxygen atom.

13. The composition of claim 9 in which the phosphoric acid compound is a phosphoric acid ester or a dithiophosphoric acid ester.

14. The composition of claim 13 in which the phosphoric acid compound is di-(2-ethylhexyl) dithiophosphoric acid, dibutyl dithiophosphoric acid, diamylphosphoric acid, diisobutyl dithiophosphoric acid, dihexylphosphoric acid, dimethyl phosphoric acid, diethyl phosphoric acid, di-n-propyl phosphoric acid, di-n-butyl phosphoric acid or dioctyl dithiophosphoric acid.

15. The composition of claim 9 in which the hydrocarbyl-substituted succinic anhydride has the following structural formula:

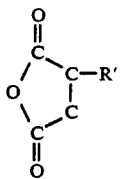

where R' is a hydrocarbyl group containing 1 to 300 carbon atoms.

16. The composition of claim 15 in which the hydrocarbyl-substituted succinic anhydride is made from a 1-olefin and maleic anhydride, the 1-olefin being ethylene, propylene, butylene, isobutylene, pentylene, heptylene, decylene, dodecylene, eicosene, higher monoolefins, polymers and copolymers derived therefrom or any of the foregoing olefins containing cyclic hydrocarbon groups such as phenyl, naphthyl or alicycle, the hydrocarbyl group having a molecular weight ranging from 50 to 2000.

17. The composition of claim 9 in which the reaction product is blended into the lubricant in an amount from at least 0.01 weight percent to 10 weight percent, based upon the total weight of the lubricant composition.

18. The composition of claim 17 in which the lubricant is a lubricating oil or grease made from a mineral oil, synthetic oil or a mixture of mineral oils and synthetic oils.

19. A method of making a lubricant composition comprising blending a major amount of a lubricant and a minor multifunctional antioxidant/antiwear amount of a reaction product made by reacting a hydrocarbon-substituted phosphoric acid and a hydrocarbon-substituted succinic anhydride to produce an intermediate which is post-reacted with a hydrocarbon-substituted organotin compound.

20. The method of claim 19 in which the organotin compound has the formula:

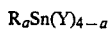

where R is a hydrocarbyl group containing 2 to 20 carbon atoms, a is an integer ranging from 1 to 3, and Y is an oxygen atom or a sulfur atom.

21. The method of claim 19 in which the organotin compound is dibutyltin oxide, dimethyltin oxide, tributyltin oxide, dioctyltin oxide or triphenyltin oxide.

22. The method of claim 19 in which the phosphoric acid is represented by the structural formula:

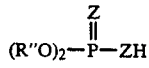

where R" is a hydrocarbyl group containing 1 to 60 carbon atoms or a hydrocarbyl group containing 2 to 60 carbon atoms and one or more heteroatoms selected from the group consisting of oxygen, sulfur or nitrogen and Z is a sulfur atom or an oxygen atom.

23. The method of claim 22 in which the phosphoric acid compound is a phosphoric acid ester or a dithiophosphoric acid ester.

24. The method of claim 23 in which the phosphoric acid compound is di-(2-ethylhexyl) dithiophosphoric acid, dibutyl dithiophosphoric acid, diamylphosphoric acid, diisobutyl dithiophosphoric acid, dihexylphosphoric acid, dimethyl phosphoric acid, diethyl phosphoric acid, di-n-propyl phosphoric acid, di-n-butyl phosphoric acid or dioctyl dithiophosphoric acid.

25. The method of claim 19 in which the hydrocarbyl-substituted succinic anhydride has the following structural formula:

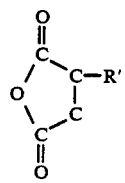

where R' is a hydrocarbyl group containing 1 to 300 carbon atoms.

26. The method of claim 25 in which the hydrocarbyl-substituted succinic anhydride is made from a 1-olefin and maleic anhydride, the 1-olefin being ethylene, propylene, butylene, isobutylene, pentylene, heptylene, decylene, dodecylene, eicosene, higher monoolefins, polymers and copolymers derived therefrom or any of the foregoing olefins containing cyclic hydrocarbon groups such as phenyl, naphthyl or alicycle, the hydrocarbyl group having a molecular weight ranging from 50 to 2000.

27. The method of claim 19 in which at least 0.01 weight percent to 10 weight percent of the additive is used based on the total weight of the lubricant composition.

28. A lubricant additive comprising a reaction product of a reaction intermediate, of a hydrocarbon substituted phosphoric acid and a hydrocarbon substituted succinic anhydride, and a hydrocarbon substituted organotin compound.

29. A method of making a lubricant additive comprising reacting a hydrocarbon substituted phosphoric acid and a hydrocarbon substituted succinic anhydride to produce a reaction intermediate; reacting the reaction intermediate with a hydrocarbon substituted organotin compound to produce the lubricant additive.

* * * * *